US00PP18739P2

(12) United States Plant Patent
Cain et al.

(10) Patent No.: US PP18,739 P2
(45) Date of Patent: Apr. 22, 2008

(54) PLUM TREE NAMED 'SUPLUMTHIRTYEIGHT'

(50) Latin Name: *Prunus salicina*
Varietal Denomination: Suplumthirtyeight

(75) Inventors: David W. Cain, Bakersfield, CA (US); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 11/586,211

(22) Filed: Oct. 24, 2006

(51) Int. Cl.
*A01H 5/00* (2006.01)

(52) U.S. Cl. ..... Plt./184
(58) Field of Classification Search ..... Plt./184
See application file for complete search history.

(56) References Cited

U.S. PATENT DOCUMENTS

PP8,363 P * 9/1993 Weinberger ..... Plt./184

* cited by examiner

*Primary Examiner*—Wendy Haas
(74) *Attorney, Agent, or Firm*—Knobbe Martens Olson & Bear, LLP

(57) ABSTRACT

A new and distinct plum tree variety, *Prunus salicina,* cv. 'Suplumthirtyeight' is characterized by ripening very early in the harvest season, about ten days earlier than 'Red Beaut' (unpatented). The new variety is further characterized by relatively large-sized fruit for the season, smooth black skin, juicy amber flesh that has a sugar content of approximately 15° brix, and early full bloom compared to 'Black Beaut' (unpatented). The winter chilling requirement is estimated to be approximately 300 hours at or below approximately 7.2° C.

1 Drawing Sheet

Latin name of the genus and species claimed: *Prunus salicina.*
Variety denomination: 'Suplumthirtyeight'.

BACKGROUND AND SUMMARY OF THE INVENTION

This invention relates to the discovery and asexual propagation of a new and distinct variety of plum, *Prunus salicina* cv. 'Suplumthirtyeight'. The new variety was first hybridized by David Cain and selected by Terry Bacon as breeder number: '97P047-010-311.' The new variety was first evaluated by Terry Bacon near Wasco, Calif. in Kern County. The variety 'Suplumthirtyeight' was originated by hybridization.

The new variety 'Suplumthirtyeight' is characterized by ripening very early in the season. The harvest season, May 12 through May 20, is about ten days earlier than that of 'Red Beaut' (unpatented) (May 22 through June 1) in the Wasco, Calif. area. The new variety 'Suplumthirtyeight' is further characterized by relatively large-sized fruit for the season (average fruit weight approximately 108 gm, compared to approximately 65 gm for 'Red Beaut'), smooth black skin, and juicy amber flesh that has a sugar content of approximately 15° brix.

The seed parent is unpatented breeding selection '92P037-130-001', and the pollen parent is 'Suplumtwenty' (the subject of U.S. Plant Pat. No. PP8363). The parent varieties were first crossed in February of 1997, with the date of planting of the progeny being February 1998, and the date of first flowering being February 2000. The new plum variety 'Suplumthirtyeight' was first asexually propagated by Terry Bacon near Wasco, Kern County, Calif. in January 2003, by budding onto 'Nemared' (unpatented) rootstock.

The new variety 'Suplumthirtyeight' is distinguished from its seed parent, '29P037-130-001' in that the new variety ripens very early (around mid-Mary), while the seed parent ripens during late June. The new variety 'Suplumthirtyeight,' also has a larger fruit size (approximately 108 gm) compared to approximately 88 gm for the seed parent.

The new variety 'Suplumthirtyeight' is distinguished from its pollen parent, 'Suplumtwenty' in that the new variety ripens very early, (around mid-May), while the pollen parent ripens during late June to early July. The new variety 'Suplumthirtyeight' also has a smaller fruit size (approximately 108 gm) compared to 195 gm for 'Suplumtwenty'.

The new variety 'Suplumthirtyeight' most closely resembles 'Black Beaut' (unpatented) in that both varieties have smooth black skin, amber flesh, and similar sugar contents (approximately 15° brix). However, the near variety 'Suplumthirtyeight' ripens very early (mid-May), about three weeks earlier than 'Black Beaut' (early- to mid-June). Full bloom of the new variety 'Suplumthirtyeight' also takes place earlier (mid-February) compared to 'Black Beaut' (early March).

The new variety 'Suplumthirtyeight' has been shown to maintain its distinguishing characteristics through successive asexual propagations by, for example, budding onto 'Nemared' rootstock.

BRIEF DESCRIPTION OF THE PHOTOGRAPH

The accompanying color photographic illustration shows typical specimens of the foliage and fruit of the present new plum variety 'Suplumthirtyeight.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly tree as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon the R.H.S. Colour Chart published by The Royal Horticultural Society, London, England.

The description matter which follows pertains to 3 year old 'Suplumthirtyeight' plants on Nemared (unpatented) rootstock, grown in the vicinity of Wasco, Kern County, Calif. during 2005, and is believed to apply to plants of the variety grown under similar conditions of soil and climate elsewhere.

TREE

General: (Measurements taken on 3 year old tree on Nemared rootstock unless otherwise noted.)

*Size.*—Medium. Normal for most plum varieties. Reaches a height of approximately 3.5 meters including normal pruning.

*Vigor.*—Moderately vigorous; growth of approximately 1.8 to 2 meters in height during the first growing season.

*Growth.*—Upright-spreading, with whippy growth that does not branch readily.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Unknown.

*Canopy density.*—Medium-dense. Pruning is required to open tree vase shape, allowing more sunlight to center of tree.

*Hardiness.*—Hardy in all fruit growing areas of California. Winter chilling requirement is approximately 300 hours at or below approximately 7.2°.

*Disease resistance/susceptibility.*—No specific testing for relative plant disease resistance/susceptibility has been designed. Under close observation in Kern County, Calif., no particular plant/fruit disease resistance/susceptibility has been observed.

Trunk: (Measurements at approximately 30 cm above soil line).

*Diameter.*—Approximately 15 cm, varies with soil type, fertility, climatic conditions and cultural practices.

*Texture.*—Medium shaggy, increases with age of tree.

*Trunk color.*—About Grey-brown 199B to Brown 200A, becomes darker with age.

Branches: (Measurements at approximately 90 cm above soil line)

*Size.*—Diameter ranged from approximately 5 to approximately 7 cm.

*Texture.*—Smooth on first year wood, increasing roughness with tree age.

*Color.*—Branches vary from about Grey-brown 199B to Brown 200A, becomes darker with age.

*Lenticels.*—Absent or very difficult to detect.

Flowering shoots: (Data taken in January at midpoint of dormancy).

*Size.*—Average diameter approximately 4 mm.

*Color.*—Topside: About Greyed-orange 166C. Underside: About Greyed-orange 168A.

*Flower shoot lenticels.*—Plentiful. Color: About Greyed-green 196C. Diameter: Approximately 0.2 mm.

*Flowering shoot leaf buds.*—Shape: Obovate. Width: Approximately 2 mm. Length: Approximately 2.8 mm. Color: About Greyed-orange 165B.

*Flowering shoot flower buds.*—Shape: Elliptic. Width: Approximately 1.5 mm. Length: Approximately 1.8 mm. Color: About Greyed-orange 177A. Number per node: Usually 2.

FOLIAGE

Leaves (Data taken in July on fully expanded leaf at midpoint of current-season growth.)

*Size.*—Average length: Approximately 103 mm, including petiole. Average width: Approximately 39 mm.

*Thickness.*—Medium.

*Color.*—Upper surface: About Yellow-green 147A. Lower surface: About Yellow-green 146B.

*Form.*—Elliptic.

*Tip.*—Acuminate.

*Base.*—Acuminate.

*Margin.*—Entire, finely crenate.

*Venation.*—Pinately net veined.

*Surface texture.*—Smooth.

Petiole:

*Average length.*—Approximately 10 mm.

*Average diameter.*—Approximately 2 mm.

*Color.*—About green 146C, becoming about red 46A.

Leaf stipules:

*Number.*—Usually 2 per leaf bud when present.

*Typical length.*—Approximately 4 mm.

Leaf glands:

*Form.*—Globose.

*Number.*—Varies from 1 to 5.

*Position.*—Alternate on upper portion of petiole and base of leaf blade.

*Average size.*—Approximately 0.7 mm by approximately 0.7 mm.

*Color.*—About green 146C.

Flowers: (Fully opened).

General:

*Flower blooming period.*—First bloom: Approximately Feb. 5, 2005. Full bloom: Approximately Feb. 10, 2005.

*Size.*—Average diameter: Approximately 26 mm.

*Flower aroma.*—Very slight.

Peduncle:

*Length.*—Approximately 7 to approximately 12 mm, average approximately 10 mm.

*Diameter.*—Approximately 1 mm.

*Color.*—About Yellow-green 144B.

Petals:

*Number.*—5.

*Arrangement.*—Free.

*Length.*—Approximately 8 to approximately 10 mm, average approximately 9 mm.

*Diameter.*—Approximately 6 mm.

*Shape.*—Elliptic.

*Apex shape.*—Rounded.
*Base shape.*—Narrows at point of attachment.
*Color.*—White.
*Surface texture.*—Smooth.
*Margins.*—slightly undulating.

Sepals:
Number.—5.
*Length.*—Approximately 2 mm.
*Diameter.*—Approximately 1.5 mm.
*Shape.*—Elliptic-triangular.
*Color.*—About Yellow-green 144B.
*Surface texture.*—Smooth.

Stamens:
*Number.*—Ranges from approximately 20 to approximately 30, average 25.
*Average length.*—Approximately 7 mm.
*Filament color.*—About White 155A.
*Anther color.*—About Greyed-yellow 162A.
*Flower pollen color.*—About Greyed-yellow 162A.

Pistil:
*Number.*—Usually one, occasionally two.
*Average length.*—Approximately 6 mm.
*Ovary diameter.*—Approximately 1 mm.
*Pubescence.*—None.
*Stigma extension in comparison to anthers.*—Below to level with anthers.

FRUIT

General: (Date taken at firm-ripe on mature tree managed to obtain maximum quality under conditions stated in Description of Variety.)
*Harvest.*—Date of first pick: Approximately May 12, 2005. Date of last pick: Approximately May 20, 2005.

Size:
*Length* (*stem end to apex*).—Approximately 55 mm.
*Diameter in line with suture plane.*—Approximately 58 mm.
*Diameter perpendicular to suture plant.*—Approximately 58 mm.
*Average weight.*—Approximately 108 gm.

Form:
*Viewed from apex.*—Rounded, symmetrical.
*Viewed from side, facing suture.*—Rounded, symmetrical.
*Viewed from side, perpendicular to suture.*—Rounded, symmetrical.

Apex shape: Slightly flattened.
Fruit stem-end cavity depth: Shallow.

Fruit stem:
*Length.*—approximately 8 mm.
*Diameter.*—Approximately 2 mm.
*Color.*—About Green 143C.

Fruit skin:
*Thickness.*—Medium.
*Adherence to flesh.*—Tenacious.
*Surface texture.*—Smooth.
*Pubescence.*—None.
*Bloom.*—Light amount.
*Ground color.*—Not visible.
*Overcolor.*—About Reddish-black 187A.
*Taste.*—Slightly tart to tart.

Flesh:
*Ripens.*—Evenly.
*Texture.*—Juicy, fine.
*Fibers.*—Few.
*Flavor.*—Bland-sweet.
*Brix.*—Approximately 15°.
*Juice.*—Abundant.
*Aroma.*—Slight.
*Color.*—The flesh is greenish-amber (about 151D) when firm, becoming amber (about 163D) when ripe.

Fruit use: Dessert. Market, local and long distance.

Fruit shipping and keeping quality: Good, holds well in cold storage for approximately 4 weeks and maintains good firmness and eating quality, minimal bruising and scarring in packing and shipping trials.

Stone: (Measurements taken on dried stones.)
*Stone freeness.*—Clingstone.
*Stone sizes.*—Length: Approximately 18 mm. Diameter in line with suture plane: Approximately 18 mm. Diameter perpendicular to suture plane: Approximately 8 mm.
*Stone form.*—Viewed from side: Rounded, symmetrical. Viewed from stem end. Flattened, symmetrical.
*Stone shape.*—Base shape: Rounded at stem attachment. Apex shape: Rounded with a small, sharp point.
*Suture surface.*—Irregularly furrowed throughout, light ridged throughout, lightly pitted throughout.
*Stone halves.*—Nearly equal.
*Stone ridges.*—About 1 to 2 on each side of the suture, small and narrow beginning at the base and extending approximately three-fourths the length of the stone.
*Stone outgrowing keel.*—Partially developed.
*Stone tendency to split.*—Slight.
*Stone color.*—About Greyed-orange 163A when dried.

What is claimed is:

1. A new and distinct plum tree as herein described and illustrated.

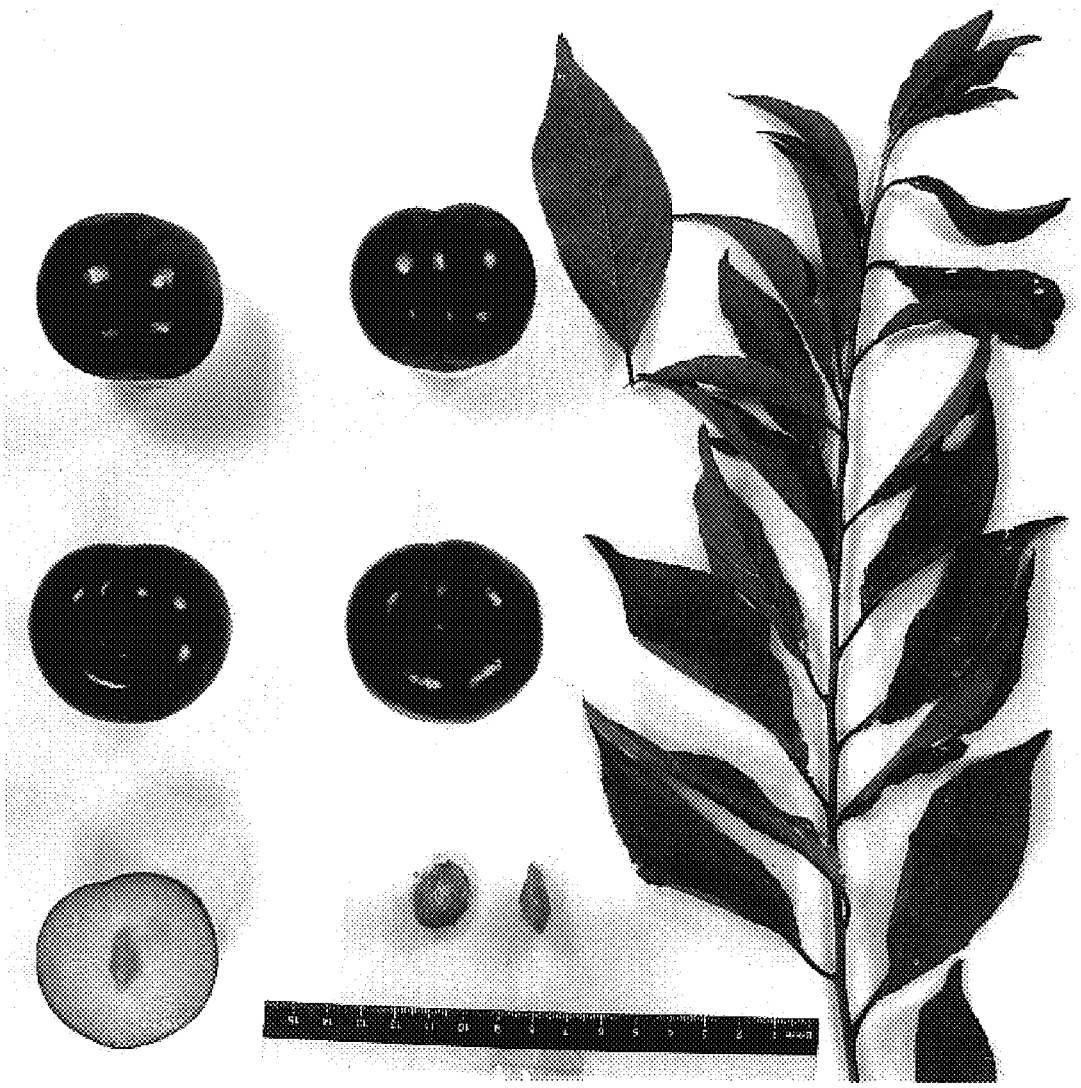

* * * * *